United States Patent
Lee et al.

(10) Patent No.: US 11,173,229 B2
(45) Date of Patent: Nov. 16, 2021

(54) PREPARATION METHOD OF INJECTABLE THERMOSENSITIVE CHITOSAN/TEMPO BASED-OXIDIZED CELLULOSE HYDROGEL

(71) Applicants: Soonchunhyang University Industry Academy Cooperation Foundation, Asan-si (KR); National Institute of Forest Science, Seoul (KR)

(72) Inventors: Byong Taek Lee, Cheonan-si (KR); Sun-Young Lee, Seoul (KR); Trang Nguyen Ho Minh, Cheonan-si (KR); Celine Abueva, Cheonan-si (KR); Sang-Jin Chun, Namyangju-si (KR); Jae-Gyoung Gwon, Seoul (KR)

(73) Assignees: SOONCHUNHYANG UNIVERSITY INDUSTRY ACADEMY COOPERATION FOUNDATION, Asan-si (KR); NATIONAL INSTITUTE OF FOREST SCIENCE, Seoul (KR)

( * ) Notice: Subject to any disclaimer, the term of this patent is extended or adjusted under 35 U.S.C. 154(b) by 0 days.

(21) Appl. No.: 15/986,985

(22) Filed: May 23, 2018

(65) Prior Publication Data
US 2019/0015550 A1 Jan. 17, 2019

(30) Foreign Application Priority Data
Jul. 12, 2017 (KR) ........................ 10-2017-0088565

(51) Int. Cl.
| | |
|---|---|
| A61L 27/26 | (2006.01) |
| A61L 27/52 | (2006.01) |
| A61L 27/20 | (2006.01) |
| A61L 27/50 | (2006.01) |
| A61L 27/54 | (2006.01) |
| A61L 27/58 | (2006.01) |

(52) U.S. Cl.
CPC ............... *A61L 27/26* (2013.01); *A61L 27/20* (2013.01); *A61L 27/50* (2013.01); *A61L 27/52* (2013.01); *A61L 27/54* (2013.01); *A61L 27/58* (2013.01); *A61L 2300/412* (2013.01); *A61L 2300/604* (2013.01); *A61L 2400/06* (2013.01); *A61L 2400/12* (2013.01); *A61L 2430/02* (2013.01); *A61L 2430/34* (2013.01)

(58) Field of Classification Search
None
See application file for complete search history.

(56) References Cited

U.S. PATENT DOCUMENTS 9,782,430 B2 * 10/2017 Ohri .................... A61K 49/048

FOREIGN PATENT DOCUMENTS

KR 10-2011-0025530 3/2011

OTHER PUBLICATIONS

Riva et al. "Cellulose-Chitosan Nanocomposites—Evaluation of Physical, Mechanical and Biological Properties" 2015.*
Injectable and biodegradable hydrogels: gelation, biodegradation and biomedical applications 2012.*
Cellulose Nanofibers Prepared by TEMPO-mediated Oxidation of Native Cellulose "Supper et al." Thermosensitive chitosan/ glycerophosphate-based hydrogel and its derivatives in pharmaceutical and biomedical applications.*
Cellulose Nanofibers Prepared by TEMPO-mediated Oxidation of Native Cellulose Supper et al. "Thermosensitive chitosan/ glycerophosphate-based hydrogel and its derivatives in pharmaceutical and biomedical applications" 2007.*
"Transparent bionanocomposite films based on chitosan and TEMPO-oxidized cellulose nanofibers with enhanced mechanical and barrier properties" 2016.*
Preparation and characterization of cellulose/chitosan blend films 2009.*
Zhang et al. Preparation and Characterization of Collagen-Chitosan Composites. 1996.*
Biocompatability and gelation of chitosan-glycerol phosphate hydrogels. 2007.*
Masruchin et al. "Characteristics of TEMPO-Oxidized cellulose fibril-based hydrogels induced by catiionic ions and their properties" 2015.*
Trang-Nguyen Ho Minh et al., "Evaluation of thermosensitive tempo-oxidized nanocellulose fiber /chitosan hydrogel as an injectable adhesion barrier post-abdominal surgery", 2016 Korea Material Society Fall Conference Korea-Japan Materials Engineering Symposium dated on Nov. 17, 2016.

* cited by examiner

*Primary Examiner* — Danah Al-Awadi
(74) *Attorney, Agent, or Firm* — Lex IP Meister, PLLC

(57) ABSTRACT

The present invention provides a method for preparing an injectable thermosensitive chitosan/TEMPO-oxidized cellulose nanofibers hydrogel. The injectable thermosensitive chitosan/TEMPO-oxidized cellulose nanofibers hydrogel exhibits superior biocompatibility through addition of TEMPO-oxidized cellulose nanofibers, and excellent cell proliferation and bone regeneration through cellular interaction, and is gelled in vivo, thus being highly useful as a filler for wound healing and bone regeneration. In addition, the injectable thermosensitive chitosan/TEMPO-oxidized cellulose nanofibers hydrogel exhibits excellent porosity, has an interconnected structure and is thermogelling, based on thermosensitivity of undergoing a sol-gel transition depending on temperature, thus inducing rapid gelation in vivo and facilitating bone regeneration upon implantation in vivo.

6 Claims, 8 Drawing Sheets

PREPARATION METHOD OF INJECTABLE THERMOSENSITIVE CHITOSAN/TEMPO BASED-OXIDIZED CELLULOSE HYDROGEL

BACKGROUND OF THE INVENTION

Field of the Invention

The present invention relates to a method for preparing an injectable thermosensitive chitosan/TEMPO-oxidized cellulose nanofibers hydrogel potentially for wound and bone healing. This hydrogel was made by adding glycerolphosphate to a mix solution of chitosan and TEMPO-oxidized cellulose nanofibers (TOCNF).

Description of the Related Art

Hydrogels are three-dimensional structural systems formed by crosslinking various hydrophilic polymer chains. Hydrogels possess prominent characteristics, such as swelling, flexibility in fabrication and modification of components, biocompatibility, and biodegradability. However, conventional pre-formed hydrogels lack versatility for use in various defect models and applications. As a result, injectable hydrogels (IHs) with better moldability capable of filling most defect areas through minimally invasive procedures have been introduced, eliminating previous drawbacks involved in common surgical implantation. Injectable hydrogel are new trend in field of regenerative medicine.

In field of regenerative medicine, natural polymers are a priority objects as biomaterials to promote new tissue formation rather than synthetic polymers because of their low cost, dynamic control of biological processes through their evolved biochemical features, and absence of an intrinsic component which is capable of exerting a para or autocrine mimicking signaling activity on cells.

Chitosan (CS) is one kind of natural polymer obtained from N-deacetylation of chitin, a mucopolysaccharide found in shells of arthropods. CS is composed of random glucosamine units and acetylglucosamine units linked by $\beta$(1-4) glycosidic bonds. CS is a hydrogel material widely used for pharmaceutical and biomedical applications due to its superb properties such as noncytoxicity, biocompatibility and biodegradability.

In addition, glycerolphosphate (GP) is a component present in the body that is not cytotoxic which is approved by the U.S. Food and Drug Administration (FDA), with the ability to differentiate human mesenchymal stem cells (MSCs) into the osteoblast lineage. Combination of chitosan (CS) and glycerolphosphate (GP) produces an injectable thermosensitive hydrogel which exists as a liquid mixture and forms a gel at 37° C. (body temperature). Injectable CS/GP hydrogel has been studied as a promising biomaterial for cell carriers in tissue engineering or drug delivery systems.

However, CS/GP in a hydrogel system still has limitation in a balance between the level of biocompatibility and thermogelling properties. Specifically, increasing concentrations of CS and GP can enhance gelation and decrease a gelation temperature to limit diffusion of the solution from the injection site or avoid the high potentiality of initial drug burst, but it also concurrently triggers difficulty in injection due to high viscosity and decreases biocompatibility. Hence, such CS/GP-based injectable thermosensitive hydrogel systems require improvement in biocompatibility and gelation efficacy.

Accordingly, as a result of repeated and thorough research to improve the thermosensitive hydrogel systems by adding other polymers to the systems, chemically modifying CS or replacing GP by other gelling factors, the present invention has been completed based on the finding that TEMPO-oxidized cellulose nanofibers (TOCNF) obtained by TEMPO-mediated oxidation of nanocellulose can improve gelation properties and biocompatibility of CS/GP-based injectable thermosensitive hydrogel system.

PRIOR ART

Patent Document (Patent Document) Korean Patent Laid-open No. 10-2011-0025530

SUMMARY OF THE INVENTION

Therefore, the present invention has been made for solving above problems, and it provides a method of preparing an injectable thermosensitive chitosan/TEMPO-based oxidized cellulose hydrogel by adding glycerolphosphate to a mix solution of chitosan and TEMPO-oxidized cellulose nanofibers (TOCNF).

The present inventors prepared an injectable thermosensitive chitosan/TEMPO-oxidized cellulose nanofibers hydrogel by firstly mixing a TOCNF solution containing TEMPO-oxidized cellulose nanofibers (TOCNF) with a chitosan solution to prepare a chitosan/TOCNF mix solution and then adding glycerolphosphate to the above mix solution. This hydrogel exhibited superior biocompatibility with decreasing toxicity of CS/GP-based hydrogel, cell proliferation and cellular interaction well. This indicated that hydrogel is effective in skin and bone regeneration. Also, it showed its sensitivity to heat when it transformed from liquid to gel in vivo at body temperature. Thus, it is useful as a filler.

In accordance with the present invention, the above and other objects can be accomplished by the provision of a method for preparing an injectable thermosensitive chitosan/TEMPO-oxidized cellulose nanofibers hydrogel including diluting a homogeneous suspension of 2,2,6,6-tetramethyl-piperidin-1-oxyl (TEMPO)-oxidized cellulose nanofibers (TOCNF) in distilled water and adding an aqueous hydrochloric acid solution to the suspension to prepare a TOCNF solution containing TEMPO-oxidized cellulose nanofibers (TOCNF), dissolving chitosan in an aqueous lactic acid solution to prepare a chitosan solution, mixing the TOCNF solution with the chitosan solution to prepare a chitosan/TOCNF solution, and adding glycerol phosphate to the chitosan/TOCNF solution to prepare an injectable thermosensitive chitosan/TEMPO-oxidized cellulose nanofibers hydrogel.

The method for preparing an injectable thermosensitive chitosan/TEMPO-oxidized cellulose nanofibers hydrogel according to the present invention includes diluting a homogeneous suspension of 2,2,6,6-tetramethyl-piperidin-1-oxyl (TEMPO)-oxidized cellulose nanofibers (TOCNF) with distilled water and adding an aqueous hydrochloric acid solution to the diluted suspension to prepare a TOCNF solution containing TEMPO-oxidized cellulose nanofibers (TOCNF).

In the present invention, the TEMPO-oxidized cellulose nanofibers may be derived from wood. Nanocellulose is a biomaterial candidate. Nanocellulose may be used in regenerative medicine such as scaffolds, for example, tissue engineered meniscus, blood vessel, ligament and tendon replacements, and in wound healing applications. This is due to excellent physical properties and specific surface chemistry of nanocellulose as well as excellent biological properties such as biodegradability, biocompatibility and low toxicity thereof.

In order to produce cellulose nanofibers, wood cellulose fibers need to be isolated. It is difficult to isolate cellulose fibers at high efficiency because they have strong fiber-fiber bonds, but uniform cellulose nanofibers can be obtained by oxidizing with the functional catalyst, 2,2,6,6-tetramethylpiperidin-1-oxy (TEMPO). The TEMPO-oxidized cellulose nanofibers (TOCNF) are derived from wood-based biomass and thus have biodegradability. In addition, TEMPO-oxidized cellulose nanofibers (TOCNF) are applicable to polymer composite materials, medical engineering materials and membranes, because they have excellent properties such as high crystallinity, excellent heat resistance and superior transparency.

TEMPO-oxidized cellulose nanofibers (TOCNF) obtained by TEMPO-mediated oxidation of nanocellulose are a new potential biological nano-material. TOCNF have high crystallinity and water solubility capable of forming hydrogels in order to create a desirable 3D environment for cell growth and differentiation.

In the present invention, 0.1% (w/v) to 0.9% (w/v) of the TEMPO-oxidized cellulose nanofibers (TOCNFs) may be contained in the TOCNF solution.

In an embodiment of the present invention, a 1% TOCNF homogeneous suspension is diluted in distilled water, adjusted pH to 2 by 1% (v/v) aqueous hydrochloric acid solution and then do ultrasonication for 30 minutes. Thereby, TOCNF solutions containing TEMPO-oxidized cellulose nanofibers (TOCNFs) at different concentrations (0.2, 0.4, 0.6 and 0.8% w/v) are made.

In the present invention, the term "suspension" means a floating system wherein fine solid particles are dispersed in a liquid.

In the present invention, the term "homogeneous" means that, although any part is taken from one substance in a certain state, it has the same physical and chemical properties as another part.

The method for preparing an injectable thermosensitive chitosan/TEMPO-oxidized cellulose nanofibers hydrogel according to the present invention includes dissolving chitosan in an aqueous lactic acid solution to prepare a chitosan solution.

In the present invention, a mix ratio (v/v) of the TOCNF solution to the chitosan solution may be 2:1 to 4:1, more specifically, 3:1.

In an embodiment of the present invention, chitosan is dissolved in an aqueous 1% (v/v) lactic acid solution to prepare a 3(w/v) chitosan (CS) solution, and the TOCNF solution and the chitosan solution are mixed at room temperature in a ratio of 3:1 (CS:TOCNF) (v:v) to prepare a chitosan/TOCNF solution. In the present invention, the chitosan (CS) is a cationic polymer electrolyte which has a pKa of about 6.5 and is dissolved only under an acidic environment. Chitosan (CS) is homogeneously dissolved in lactic acid as a solvent.

The method for preparing an injectable thermosensitive chitosan/TEMPO-oxidized cellulose nanofibers hydrogel according to the present invention also includes adding glycerolphosphate to the chitosan/TOCNF mix solution to prepare the injectable thermosensitive chitosan/TEMPO-oxidized cellulose nanofibers hydrogel.

In the present invention, the glycerol phosphate may be present in an amount of 15% (w/v) to 25% (w/v), more specifically, 20% (w/v), in the injectable thermosensitive chitosan/TEMPO-oxidized cellulose nanofibers hydrogel.

In the present invention, the chitosan may be present in an amount of 1.5% (w/v) to 3(w/v), more specifically, 2.25% (w/v) in the injectable thermosensitive chitosan/TEMPO-oxidized cellulose nanofibers hydrogel.

In an embodiment of the present invention, a chilled 60% (w/v) β-glycerol phosphate (GP) solution is added dropwise to the cooled CS/TOCNF solution under continuous stirring at 4° C. in an ice bath for about 20 minutes to prepare the injectable thermosensitive chitosan (CS)/TEMPO-oxidized cellulose nanofibers (TOCNF) hydrogel (hereinafter, simply referred to as a "CS/TOCNF hydrogel").

In the present invention, the final concentrations of CS and GP contained in the finally prepared injectable thermosensitive chitosan (CS)/TEMPO-oxidized cellulose nanofibers (TOCNF) hydrogel were 2.25% (w/v) and 20% (w/v), respectively. The injectable thermosensitive chitosan (CS)/TEMPO-oxidized cellulose nanofibers (TOCNF) hydrogel was stored in a liquid phase at 4° C. until use.

The injectable thermosensitive chitosan/TEMPO-oxidized cellulose nanofibers hydrogel according to the present invention has thermosensitivity of undergoing a sol-gel transition depending on temperature and is thus gelled in vivo at a body temperature when applied as a biomaterial in vivo.

In addition, the injectable thermosensitive chitosan/TEMPO-oxidized cellulose nanofibers hydrogel is a biodegradable material and has thermosensitivity of undergoing a sol-gel behavior depending on temperature, such that it can be easily injected as a solution into the body and can form a three-dimensional gel within a short time due to body temperature.

The injectable thermosensitive chitosan/TEMPO-oxidized cellulose nanofibers hydrogel prepared by the method may be a gel at 30° C. to 37° C., more specifically 37° C.

In an embodiment of the present invention, the injectable thermosensitive chitosan/TEMPO-oxidized cellulose nanofibers hydrogel (CS/TOCNF hydrogel) is a transparent liquid solution at 4° C. and becomes turbid and changes into a solid gel when temperature is elevated to 37° C., which indicates that gelation effectively occurs in vivo at 37° C., human body temperature. In addition, gelation speed increases as the concentration of TOCNF in the hydrogel increases.

Moreover, the injectable thermosensitive chitosan/TEMPO-oxidized cellulose nanofibers hydrogel (CS/TOCNF hydrogel) according to the present invention may be biodegradable.

In an embodiment of the present invention, adding TOCNF to a CS hydrogel facilitates decomposition of CS hydrogels by lysozymes, so that the hydrogel can be degraded under conditions similar to in vivo environments, indicating that the CS hydrogel can be effectively degraded even after implantation in vivo.

Also, the injectable thermosensitive chitosan/TEMPO-oxidized cellulose nanofibers hydrogel (CS/TOCNF hydrogel) has a porous structure.

In an embodiment of the present invention, as the concentration of TOCNF in the CS/TOCNF hydrogel increases, the surface becomes less rough, less compact and more porous.

In an embodiment of the present invention, scanning microscopy results of the CS/TOCNF revealed, for a CS/TOCNF 0.4 hydrogel including a TOCNF solution containing 0.4% (w/v) of the TEMPO-oxidized cellulose nanofibers (TOCNF), nanoparticles were almost uniform in size, were not stuck together and were evenly distributed on the surface, unlike different concentrations of CS/TOCNF hydrogels, indicating that the CS/TOCNF 0.4 hydrogel is the most optimal hydrogel shape.

Furthermore, in an embodiment of the present invention, improvement in biocompatibility of the TOCNF-added CS hydrogel was observed in vitro, and for the CS/TOCNF 0.4 hydrogel including a TOCNF solution having 0.4% (w/v) of TEMPO-oxidized cellulose nanofibers (TOCNF), cells were the most suitable for growth, adhesion and spreading.

In addition, in an embodiment of the present invention, CS/TOCNF in vivo has more infiltration and cell matrix formation, than CS hydrogels, in particular, the CS/TOCNF 0.4 hydrogel has the best tissue compatibility.

Accordingly, the injectable thermosensitive chitosan/TEMPO-oxidized cellulose nanofibers hydrogel exhibits superior biocompatibility, cell proliferation and skin and bone regeneration efficacies through cellular interaction, thus being useful as a bone filler. In addition, the injectable thermosensitive chitosan/TEMPO-oxidized cellulose nanofibers hydrogel exhibits excellent porosity, has an interconnected structure and is thermogelling, thus inducing rapid gelation in vivo and facilitating regeneration of tissues when implanted in vivo.

In another aspect of the present invention, provided is a filler for wound healing and bone regeneration including the injectable thermosensitive chitosan/TEMPO-oxidized cellulose nanofibers hydrogel prepared by the method.

As described above, the injectable thermosensitive chitosan/TEMPO-oxidized cellulose nanofibers hydrogel effectively promotes wound and bone healing and is thus useful as a filler for bone regeneration and wound healing.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Hereinafter, examples of the present invention will be described with reference to the annexed drawings in detail to such an extent that a person having ordinary knowledge in the art to which the present invention pertains can easily implement the examples. However, the present invention can be realized in various forms and is not limited to the examples described herein.

EXAMPLE 1

Preparation of CS/TOCNF Hydrogel

Figure 1:
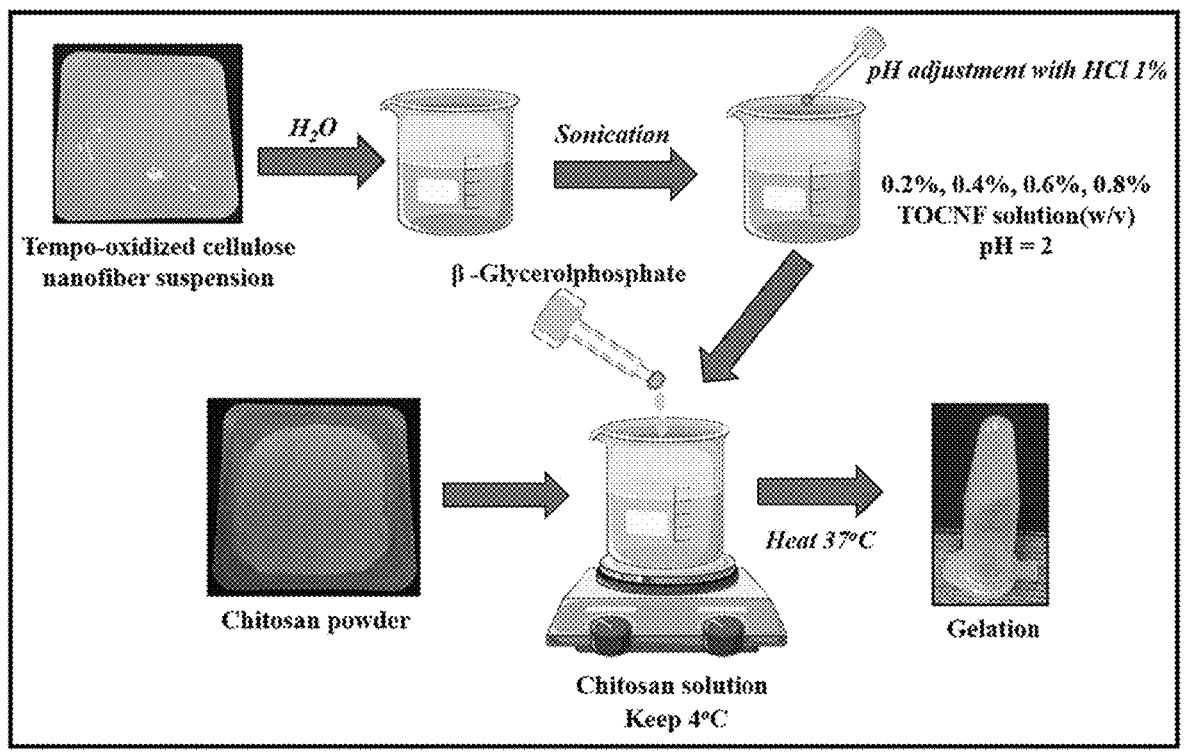
FIG. 1 is a schematic diagram showing synthesis of CS/TOCNF hydrogel.

In the present invention, a chitosan (CS)/2,2,6,6-tetramethyl-piperidin-1-oxyl (TEMPO)-oxidized cellulose nanofibers (TOCNF) hydrogel was prepared through the following process in accordance with the schematic diagram of CS/TOCNF hydrogel synthesis shown in FIG. 1.

Specifically, a 1% TOCNF homogeneous suspension was diluted with distilled water, and a 1% (v/v) aqueous hydrochloric acid solution was added to the diluted suspension while conducting ultrasonication for 30 minutes to adjust pH to 2 and thereby TOCNF solutions containing TEMPO-oxidized cellulose nanofibers (TOCNF) at different concentrations (0.2, 0.4, 0.6, 0.8% w/v) is prepared.

Then, chitosan was dissolved in an aqueous 1% (v/v) lactic acid solution to prepare a 3(w/v) chitosan (CS) solution, and then it was mixed with the TOCNF solution at room temperature in a ratio of 3:1 (CS:TOCNF) (v:v) to prepare a chitosan/TOCNF mix solution. Chitosan (CS) is a cationic polymer electrolyte which has a pKa of about 6.5 and is dissolved only under an acidic environment. Chitosan (CS) was homogeneously dissolved in lactic acid as a solvent.

Finally, 60% (w/v) of a chilled glycerolphosphate (GP) solution was added dropwise to the CS/TOCNF solution which was cooled while continuously stirring in an ice bath for about 20 minutes to prepare a chitosan (CS)/TEMPO-oxidized cellulose nanofibers (TOCNF) hydrogel.

The final concentrations of CS and GP contained in the finally prepared injectable thermosensitive chitosan (CS)/TEMPO-oxidized cellulose nanofibers (TOCNF) hydrogel were 2.25% (w/v) and 20% (w/v), respectively. The CS/TOCNF hydrogel was stored in a liquid phase at 4° C. In addition, the prepared CS/TOCNF hydrogel was gelled at 37° C.

EXAMPLE 2

Analysis of Gelation of CS/TOCNF Hydrogel

Figure 2:
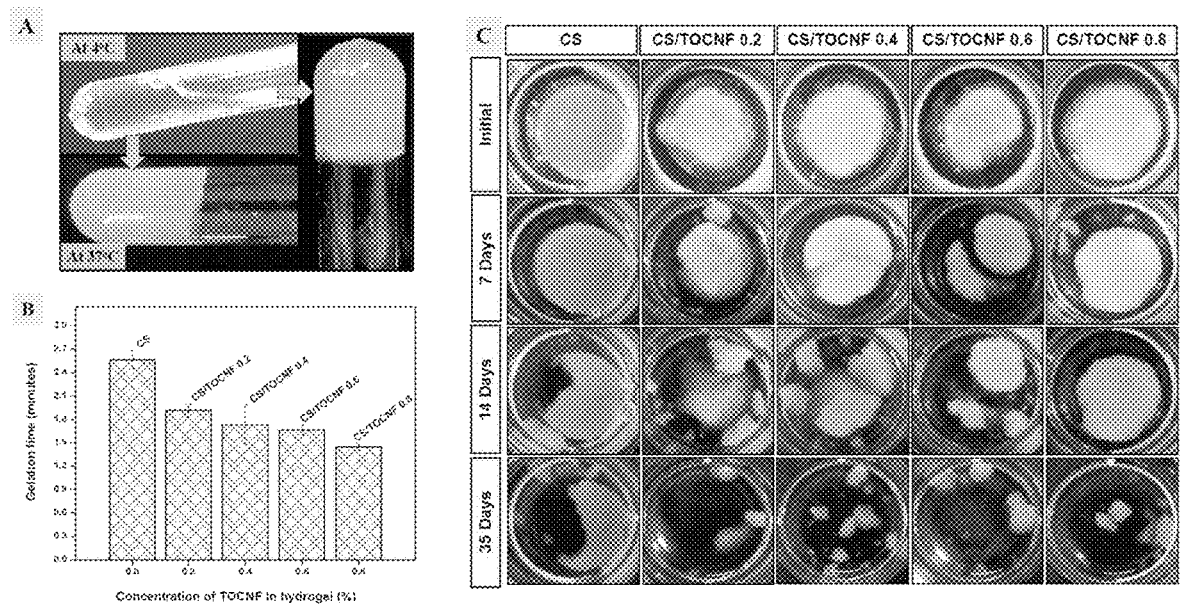
FIG. 2 shows (A) an optical image of thermosensitive CS/TOCNF hydrogel sol-gel transition, (B) a gelation time of CS and varying CS/TOCNF hydrogels at 37° C. and (C) degradation profiles for hydrogels immersed in PBS containing a lysozyme enzyme (1 mg/ml)

FIG. 2 shows (A) an optical image of a thermosensitive CS hydrogel, (B) a gelation time of CS and varying CS/TOCNF hydrogels at 37° C., and (C) degradation profiles for the hydrogels immersed in PBS containing a lysozyme enzyme (1 mg/ml).

Specifically, as shown in FIG. 2A, hydrogel at 4° C. was a transparent liquid solution which could flow easily when the tube was tilted, but it became more turbid and stopped to flow when the temperature was increased to 37° C. The change in turbidity of the hydrogel is recognized as a criterion for sol-gel transition of hydrogel in the gelation process. All hydrogels showed the same change of sol-gel status in the gelation progress.

Gelation time of hydrogel was measured at physiologic temperature (37° C.). As shown in FIG. 2B, when the concentration of TOCNF in CS hydrogel was increased from 0% to 0.8% (0, 0.2, 0.4, 0.6, and 0.8%), the gelation time of hydrogel was gradually decreased. There among, the gelation time of CS hydrogel without any addition of TOCNF was the longest, while that of the CS hydrogel with 0.8% TOCNF was the shortest. These results demonstrated that the addition of TOCNF to the CS hydrogel could increase the speed of hydrogel gelation. The concentration of TOCNF in the hydrogel is inversely proportional to gelation time.

In addition, gelation time was shortened within an allowed limit for suitable injection. Viscosity of hydrogels did not become thick suddenly. The formation of gel was not excessively rapid, so needle clogging did not occur during the process of in vivo testing. However, injecting hydrogel became harder, because the solution became denser as the content of TOCNF increased. The present inventors also observed that the combination of TOCNF with CS made the solution more viscous, while gelling faster. That is, adding TOCNF to the CS hydrogel increased the viscosity of the solution, thus accelerating the gelation process.

EXAMPLE 3

Analysis of Degradation Profiles of CS/TOCNF Hydrogels

FIG. 2C shows degradation profiles for hydrogels immersed in PBS containing a lysozyme enzyme (1 mg/ml). Increasing TOCNF content in hydrogels caused the chitosan crystalline structure to become weaker, making the surface of such CS/TOCNF gel looser, more porous and more easily degraded during in vitro incubation compared to CS gel. Changing shape and size of hydrogels after 7, 14, and 35 days of immersion in PBS containing lysozyme are shown in FIG. 2C. Most CS/TOCNF hydrogels were degraded and only a small portion remained after 35 days of incubation. In contrast, CS hydrogel was only degraded to half after 35 days of incubation. These results suggest that addition of TOCNF contributed to faster degradation of CS hydrogel, so that it can be degraded under conditions similar to in vivo environments, indicating that the CS/TOCNF hydrogel can be effectively degraded even after implantation in vivo.

EXAMPLE 4

Evaluation of Morphology of CS/TOCNF Hydrogel

Figure 3:
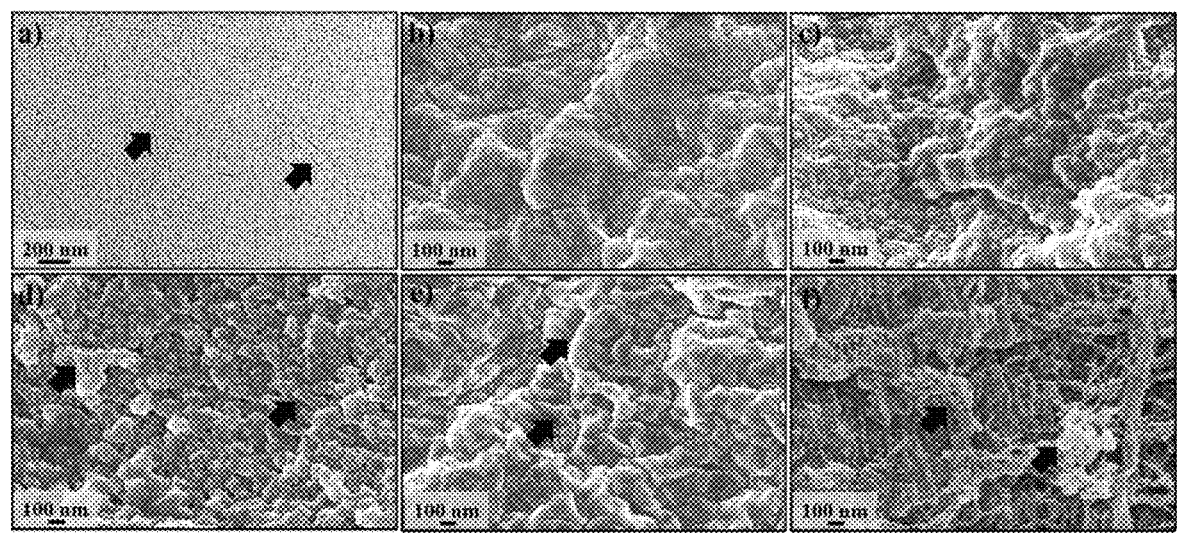
FIG. 3 shows (a) a transmission electron microscopy (TEM) image of TEMPO-oxidized cellulose nanofibers (TOCNF). Scanning electron microscopy (SEM) micrographs with magnification 35000× of chitosan, CS (b) and CS/TOCNF set hydrogels containing different concentrations of TOCNF: (c) CS/TOCNF 0.2; (d) CS/TOCNF 0.4; (e) CS/TOCNF 0.6; and (f) CS/TOCNF 0.8. Orange arrows indicate TEMPO-oxidized cellulose nanofibers and yellow arrows indicate nanoparticles formed through gelation.

FIG. 3 shows (a) transmission electron microscopy (TEM) images of TEMPO-oxidized cellulose nanofibers (TOCNF) and scanning electron microscopy (SEM) micrographs of chitosan CS (b) and CS/TOCNF set hydrogels containing different concentrations of TOCNF: (c) CS/TOCNF 0.2; (d) CS/TOCNF 0.4; (e) CS/TOCNF 0.6; and (f) CS/TOCNF 0.8. Orange arrows indicate TEMPO-oxidized cellulose nanofibers and yellow arrows indicate nanoparticles formed through gelation.

Referring to FIG. 3, hydrogel morphology was significantly impacted when TOCNF was added to the CS hydrogel. SEM micrographs of hydrogels demonstrated that hydrogel morphology depended on the concentration of TOCNF added to the CS hydrogel (FIGS. 3b-3f). Specifically, the surface of the CS hydrogel without any addition of TOCNF was rough and compact. However, surfaces of CS/TOCNF hydrogels became looser and more porous in proportion to TOCNF concentration (the higher the TOCNF concentration, the looser and more porous the surface). It was clearly seen that nanoparticles synthesized by the gelation mechanism grew increasingly. The size of these nanoparticles varied. Their shapes also changed in the longitudinal direction of TOCNF fibers. For CS/TOCNF 0.4 hydrogels, nanoparticles were most uniform in size. These nanoparticles were not stuck together. Instead, they were evenly distributed on the surface, unlike the other concentrations of CS/TOCNF hydrogels.

EXAMPLE 5

FTIR and XRD Analysis of CS/TOCNF Hydrogels

Figure 4:
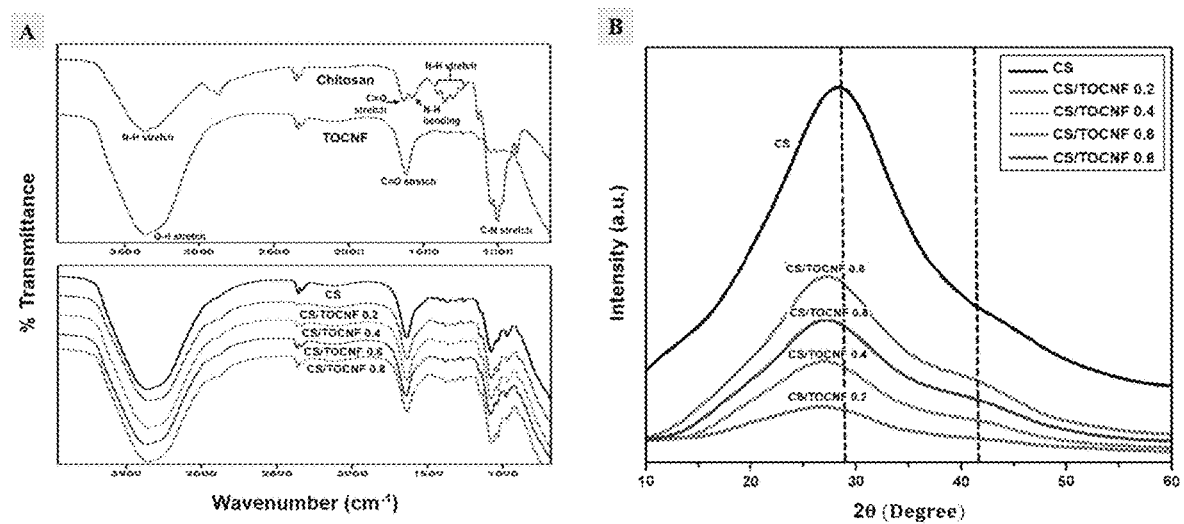
FIG. 4 shows (A) Fourier transform infrared (FT-IR) spectra of TEMPO-oxidized cellulose nanofibers (TOCNF) and chitosan (CS) raw materials, CS and CS/TOCNF set hydrogels containing different concentrations of TOCNF.(B) X-ray diffraction (XRD) spectra of CS and CS/TOCNF set hydrogels.

In addition, the formation of CS/TOCNF hydrogels was analyzed by FTIR testing. FIG. 4 shows (A) Fourier transform infrared (FT-IR) spectra of TEMPO-oxidized cellulose nanofibers (TOCNF) and chitosan (CS) raw materials, CS and CS/TOCNF set hydrogels containing different concentrations of TOCNF and (B) X-ray diffraction (XRD) spectra of CS and CS/TOCNF set hydrogels. FTIR spectra of raw materials such as chitosan (CS) and TEMPO-oxidized cellulose nanofibers (TOCNF) and all CS/TOCNF hydrogels are shown in FIG. 4A. Spectra of hydrogels were similar to each other. They had some minor differences when compared to spectra of raw materials. This indicated that, although CS/TOCNF hydrogels formed new structures, structural characteristics of the two raw components remained. In a spectrum region from 2,000 $cm^{-1}$ to 3,950 $cm^{-1}$ of hydrogels, N—H stretching band (3,363 $cm^{-1}$) and C=Oband of the amide group CONHR (2,875 $cm^{-1}$) were observed. O—H stretch band (3,361 $cm^{-1}$) reduced slightly. In other spectrum regions (680 $cm^{-1}$ to 2,000 $cm^{-1}$), the C=O band of the proton amide group (1,633 $cm^{-1}$) in hydrogels was strong compared to that of raw chitosan. However, it was weaker compared to raw TOCNF. The group of bands from 680 $cm^{-1}$ to 1,600 $cm^{-1}$ of raw chitosan representing amidic groups (Amide II, Amide III and Amide VI) were declined significantly in the spectra of hydrogels. This demonstrated that new hydrogen bonds could be formed between C=O of CS and O—H of GP, the junction of N—H of CS and CS, and the junction of N—H of CS and O—H. This resulted in reduced CS solubility and formation of hydrophilic and hydrophobic domains. This might have caused sol-gel transition.

As FTIR could not reveal differences between CS/TOCNF and CS/GP hydrogels, X-ray diffraction studies were performed to examine difference in crystalline structure between CS and CS/TOCNF hydrogels. CS hydrogel exhibited only one peak at 2θ of about 30° in XRD patterns (FIG. 4B), while the CS/TOCNF hydrogel showed two prominent peaks. One peak was similar to the peak of CS hydrogels, but had lower intensity and slightly lower 2θ. The other peak was considerably weak at 2θ of about 40°, representing a chemical functional group that was shown only in TOCNF. Intensities of these peaks of CS/TOCNF hydrogels were increased when TOCNF content in CS hydrogel was increased except for CS/TOCNF 60 which had the highest intensity.

EXAMPLE 6

In Vitro Biocompatibility Experimentation

In the process of producing biomedical materials, evaluation of biocompatibility is necessary to determine whether a foreign material implanted into the body can exist in harmony with tissues without causing deleterious changes. Biocompatibility was assessed in this study both in vitro and in vivo. L929 fibroblast and pre-osteoblast MC3T3-E1 cells, which are two popular cell lines studied widely for wound healing and bone regeneration, were used in the present experiment to assess the biocompatibility of CS/TOCNF hydrogels.

Figure 5:
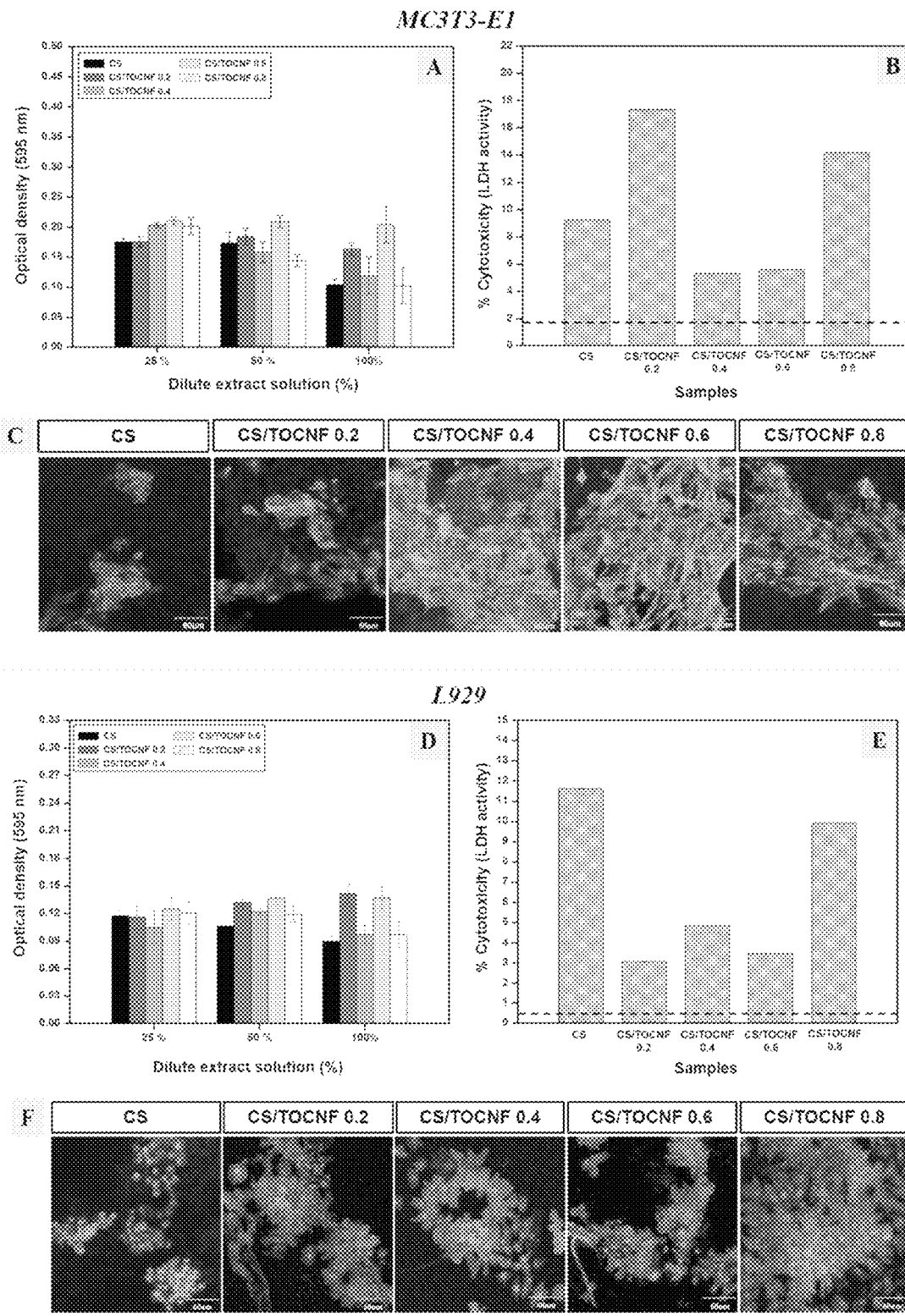
FIG. 5 shows in vitro biocompatibility determination by MTT assay and LDH cytotoxicity assay, and cell proliferation behavior observed through confocal microscopy of pre-osteoblast MC3T3-E1 (A, B and C) and fibroblast L929 (D, E and F) cell lines on the CS and CS/TOCNF set hydrogels incubated for 7 days at 37° C., 5% $CO_2$. The values plotted are averages of six replicates with SD.

FIG. 5 shows in vitro biocompatibility determination by MTT assay and LDH cytotoxicity assay, and cell adhesion behavior observed through confocal microscopy of pre-osteoblast MC3T3-E1 (A, B and C) and fibroblast L929 (D, E and F) cell lines on CS and CS/TOCNF set hydrogels incubated for 7 days at 37° C., 5% $CO_2$. The values plotted are averages of six replicates with SD.

Cell viability was assessed mainly through MTT assay (living cell rate) and LDH assay (dead cell rate). Results from MTT assay generally showed that MC3T3-E1 or L929 cells grew better with the presence of TOCNF in CS hydrogel at all kinds of extracted dilutions. The rate of dead cells of both types of cells on hydrogels was low (<20%) based on LDH assay.

LDH assay showed that MC3T3-E1 cells exhibited low cytotoxicity at CS/TOCNF 0.4% and CS/TOCNF 0.6%. L929 cells also exhibited low cytotoxicity and excellent cell growth at hydrogels containing 0.2% to 0.6% of TOCNF. L929 cells exhibited low cytotoxicity and excellent cell growth at hydrogels containing 0.2% to 0.6% of TOCNF. Both MTT assay (FIG. 5D) and LDH assay (FIG. 5E) of L929 cells confirmed similar results.

Adhesion behaviors of L929 and MC3T3-E1 cells were reviewed at 7 days after cells were seeded onto the surface of hydrogels. FIG. 5C (MC3T3-E1 cells) and FIG. 5F (L929 cells) showed that these cells very well attached to these hydrogels. The cells spread flat on the surface of CS/TOCNF 0.4 and CS/TOCNF 0.8 with the presence of actin filaments which were stained by fluorescein isothiocyanate conjugated phalloidin (FITC). However, L929 cells tend to grow around areas with TOCNF and form colonies on the surface of hydrogel. It could be seen that addition of TOCNF improved biocompatibility of CS hydrogel toward fibroblastic type of cells, although its influence was absolutely different depending on the type of cells and level of TOCNF added to the CS hydrogels. Diverse cellular responses to hydrogels were partly due to the combination of positively charged CS and negatively charged TOCNF that unpredictably changed gel surface conductivity. As can be seen from synthesized results in vitro, concentration of TOCNF at 0.4% was the most suitable for both types of cells to develop, attach and spread.

EXAMPLE 7

In Vivo Biocompatibility Test

Then, in vivo bio-compatibility testing was conducted using the produced CS/TOCNF biomaterials. In vivo testing is the last step to examine the exact response of human body to the materials after initial in vitro evaluation for biocompatibility.

Figure 6:
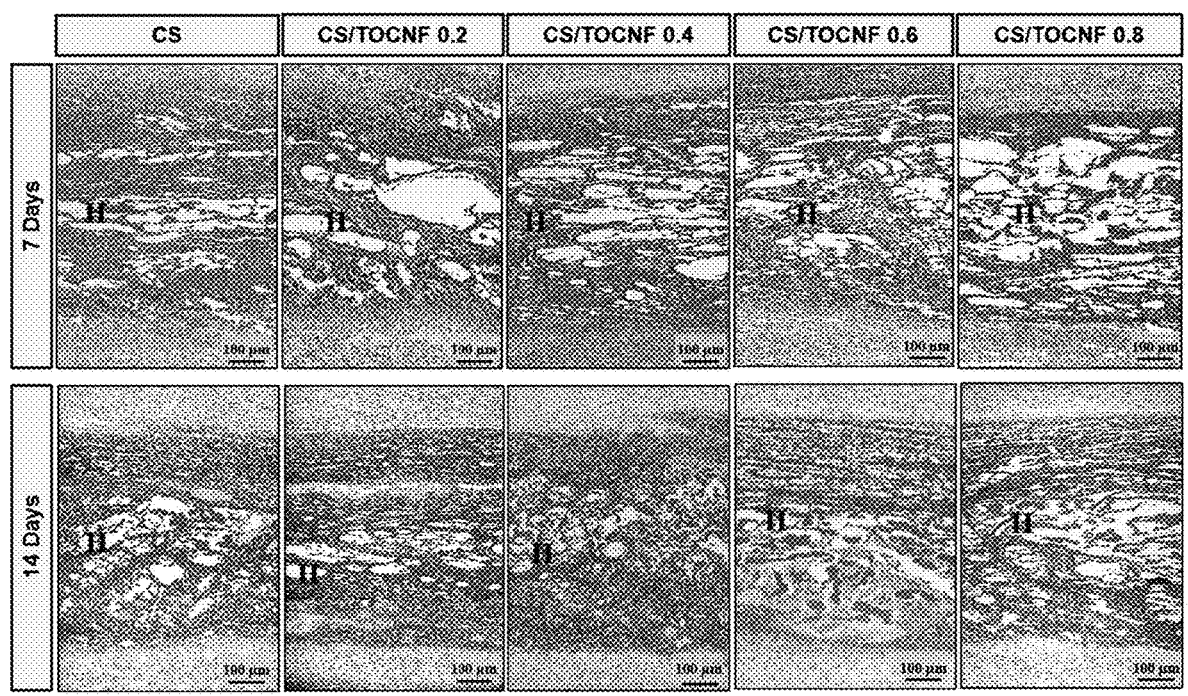
FIG. 6 shows Hematoxylin and Eosin (H&E) stained tissue sections of subcutaneously injected CS and CS/TOCNF hydrogels in Sprague Dawley rats showing hydrogel morphology and inflammatory response towards implant samples after 7 and 14 days of implantation.

FIG. 6 shows Hematoxylin and Eosin (H&E) stained tissue sections of CS and CS/TOCNF hydrogels subcutaneously injected into Sprague Dawley rats showing hydrogel morphology and inflammatory response to implant samples on 7 and 14 days after hydrogel implantation.

Based on H&E staining, morphologies of hydrogels were different. As shown in FIG. 6, these hydrogels could not be degraded completely within 2 weeks, similar to in vitro results. Within the first week after subcutaneous injection of hydrogels into rats, the first stage of inflammatory response occurred and all hydrogels were encapsulated by cellular layers. Encapsulated areas showed dark purple color. It was the darkest for CS hydrogel and CS/TOCNF 0.2 hydrogel.

Figure 7:
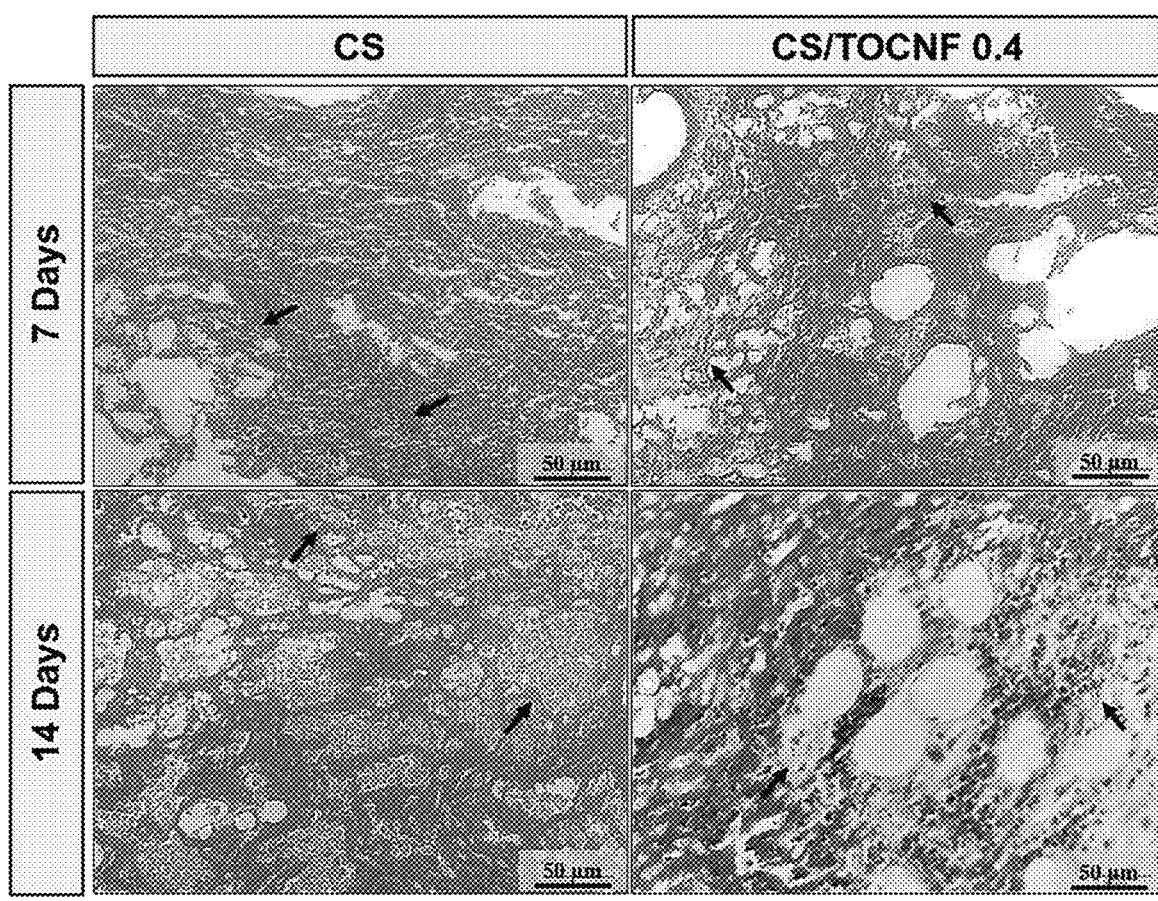
FIG. 7 shows high magnification images of H&E stained CS and CS/TOCNF 0.4 tissue sections with cell infiltration and cell matrix formation (indicated by arrows) observed within the hydrogel samples.

FIG. 7 shows high magnification images of H&E stained CS and CS/TOCNF 0.4 (selected samples) tissue sections with cell infiltration and cell matrix formation (indicated by arrows) observed within the hydrogel samples.

After the second week, encapsulation of hydrogels was remarkably developed with arrangement of connective tissues. The color of an encapsulated area became lighter. When the central regions of CS/TOCNF 0.4 and CS hydrogel were observed, the numbers of infiltrated cells and created cell matrixes were increased dramatically from the first week to the second week in both hydrogels, especially for CS/TOCNF 0.4 which had infiltrated cells and matrixes higher than the CS hydrogel (FIG. 7).

Figure 8:
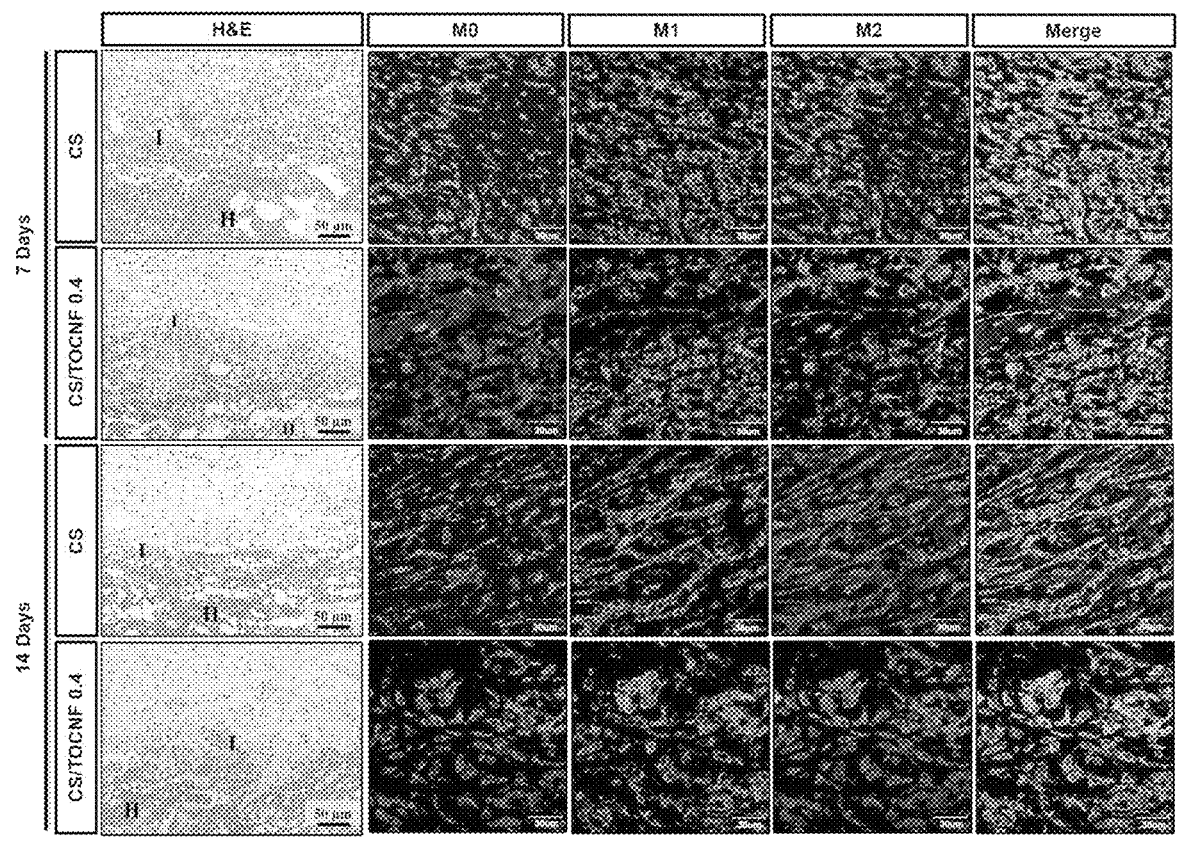
FIG. 8 shows immunofluorescence staining showing the presence of M2 types of macrophage cells surrounding implanted CS and CS/TOCNF 0.4 samples after 7 and 14 days of implantation. Pan macrophage, M0 (blue), M1 (red) and M2 (green) type of macrophage. The hydrogel sample area H and interface I are shown.

Then, tissue sections were subjected to immunofluorescence staining to check types of activated macrophage cells surrounding the implanted hydrogels. As shown in FIG. 8, pan macrophage (M0 blue) was found to be decreased in quantity from the first week to the second week. Alternatively activated macrophages (M2 green-repair) were intensified in CS hydrogel and CS/TOCNF 0.4 hydrogel on the second week. On the contrary, classically activated macrophages (M1 red—proinflammatory) were reduced. Alternatively activated macrophages of CS/TOCNF 0.4 were much more than those of CS hydrogel (FIG. 8—Merge). Also, immunofluorescence staining images clearly showed that CS/TOCNF 0.4 in the second week showed reduction in macrophages, as compared to CS hydrogel.

Results of subcutaneous injection in vivo showed that hydrogels caused an inflammatory response in the body, based on the presence of macrophages. This is normal in the initial stage after subcutaneous injection because the body will react to foreign materials injected into the body. The presence of macrophages indicates both inflammatory immune response and the ability of tissue remodeling. After 2 weeks, the quantity of macrophages was decreased and the quantity of alternatively activated macrophages was increased without any symptoms such as pus or allergy, which means that rats have good health conditions. This indicates that CS/TOCNF 0.4 hydrogel has in vivo acceptable tissue compatibility.

The present invention relates to a method for preparing an injectable thermosensitive chitosan/TEMPO-oxidized cellulose nanofibers hydrogel. TOCNF facilitates the sol/gel transition, forms a looser and more porous hydrogel surface, and is more suitable for cell infiltration in vivo. CS/TOCNF hydrogels exhibits better growth and adhesion of L929 fibroblast and pre-osteoblast MC3T3-E1 cells than CS hydrogel. Especially, a CS/TOCNF hydrogel containing a 0.4% (w/v) TOCNF solution exhibits the best cell adhesion and growth. Although hydrogels causes inflammatory response after injected into Sprague Dawley rats, the presence of alternatively activated macrophages increased after 2 weeks demonstrate that CS/TOCNF 0.4 is suitable for regenerating tissues.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for preparing an injectable thermosensitive chitosan/TEMPO-oxidized cellulose nanofibers hydrogel comprising:
    diluting a homogeneous suspension of 2,2,6,6-tetramethyl-piperidin-1-oxyl (TEMPO)-oxidized cellulose nanofibers (TOCNFs) in distilled water and adding an aqueous hydrochloric acid solution to the diluted suspension to prepare a TOCNF solution containing TEMPO-oxidized cellulose nanofibers (TOCNFs);
    dissolving chitosan in an aqueous lactic acid solution to prepare a chitosan solution;
    mixing the TOCNF solution with the chitosan solution to prepare a chitosan/TOCNF mix solution; and
    adding glycerolphosphate to the chitosan/TOCNF mix solution to prepare the injectable thermosensitive chitosan/TEMPO-oxidized cellulose nanofibers hydrogel,
    wherein the TEMPO-oxidized cellulose nanofibers (TOCNF) are present in an amount of 0.4% (w/v) in the chitosan/TEMPO-oxidized cellulose nanofibers hydrogel,
    wherein the TOCNF solution and the chitosan solution are mixed in a mix ratio (v/v) of 3:1,
    wherein the chitosan is present in an amount of 2.25% (w/v) in the injectable thermosensitive chitosan/TEMPO-oxidized cellulose nanofibers hydrogel.

2. The method according to claim 1, wherein the injectable thermosensitive chitosan/TEMPO-oxidized cellulose nanofibers hydrogel undergoes sol-gel transition depending on temperature.

3. The method according to claim 1, wherein the injectable thermosensitive chitosan/TEMPO-oxidized cellulose nanofibers hydrogel is gelled in vivo.

4. The method according to claim 1, wherein the injectable thermosensitive chitosan/TEMPO-oxidized cellulose nanofibers hydrogel has a porous structure.

5. The method according to claim 1, wherein the glycerolphosphate is present in an amount of 15% (w/v) to 25% (w/v) in the injectable thermosensitive chitosan/TEMPO-oxidized cellulose nanofibers hydrogel.

6. The method according to claim 1, wherein the injectable thermosensitive chitosan/TEMPO-oxidized cellulose nanofibers hydrogel facilitates bone regeneration.

* * * * *